United States Patent [19]

Kaufman

[11] Patent Number: 4,866,997
[45] Date of Patent: Sep. 19, 1989

[54] GRAIN PROBE

[76] Inventor: Kevin W. Kaufman, 301 Hollowood Dr., West Lafayette, Ind. 47906

[21] Appl. No.: 140,676

[22] Filed: Jan. 4, 1988

[51] Int. Cl.⁴ .................... G01N 1/12; G01N 1/08; G01K 13/12; G01K 13/02
[52] U.S. Cl. ...................... 73/864.63; 73/864.64; 374/155; 374/157
[58] Field of Search ............ 73/864.63, 864.64, 864.65, 73/864.66; 374/155, 157

[56] References Cited

U.S. PATENT DOCUMENTS

| | | |
|---|---|---|
| 646,217 | 3/1900 | Hollingsworth . |
| 1,072,644 | 9/1913 | Peck . |
| 2,184,472 | 12/1939 | Sand . |
| 2,331,227 | 10/1943 | Proudlock . |
| 2,523,691 | 9/1950 | Fitch . |
| 3,153,344 | 10/1964 | Lawrence et al. . |
| 3,192,773 | 7/1965 | Wilson .......................... 73/864.64 X |
| 3,199,353 | 8/1965 | Burnight . |
| 4,044,607 | 8/1977 | Deal .............................. 73/73 |
| 4,072,059 | 2/1978 | Hamilton . |
| 4,179,930 | 12/1979 | Chrisp . |
| 4,248,089 | 2/1981 | Heinmets . |
| 4,283,946 | 8/1981 | Bowser et al. ................. 73/864.31 |
| 4,399,404 | 8/1983 | Resh ............................. 324/61 R |
| 4,790,198 | 12/1988 | Awtry ............................ 73/864.64 |

FOREIGN PATENT DOCUMENTS

| | | | |
|---|---|---|---|
| 640304 | 4/1962 | Canada ............................ | 73/864.64 |
| 502276 | 2/1976 | U.S.S.R. .......................... | 73/864.63 |

OTHER PUBLICATIONS

Delmhorst Instrument Company, Boonton, N.J., Electric Thermometer, Model TM-2B, Rel. 6413-983 (article); 2 pages.
Seedburo Equipment Company, Chicago, Illinois, catalog pp. 27–30, both published by Dec. 1987.

Primary Examiner—Tom Noland
Attorney, Agent, or Firm—Woodard, Emhardt, Naughton Moriarty & McNett

[57] ABSTRACT

A grain probe for sampling and measuring the physical characteristics of stored grain in situ. The probe has a telescopic shaft with a meter fixedly attached to one end thereof and a novel grain probe tip fixedly attached to the opposite end thereof, a grain receiving chamber within the tip, an environmental measuring element is affixed within the grain receiving chamber and is directly coupled to a readout meter; and there is provided a novel mechanism for automatically closing the grain receiving chamber to grain kernels while the probe tip is being inserted into stored grain and automatically opening the grain receiving chamber to grain kernels for sampling and direct contact with the environmental measuring element to provide instantaneous physical characteristic information as the probe tip is slightly withdrawn from the stored grain.

16 Claims, 1 Drawing Sheet

U.S. Patent    Sep. 19, 1989    4,866,997
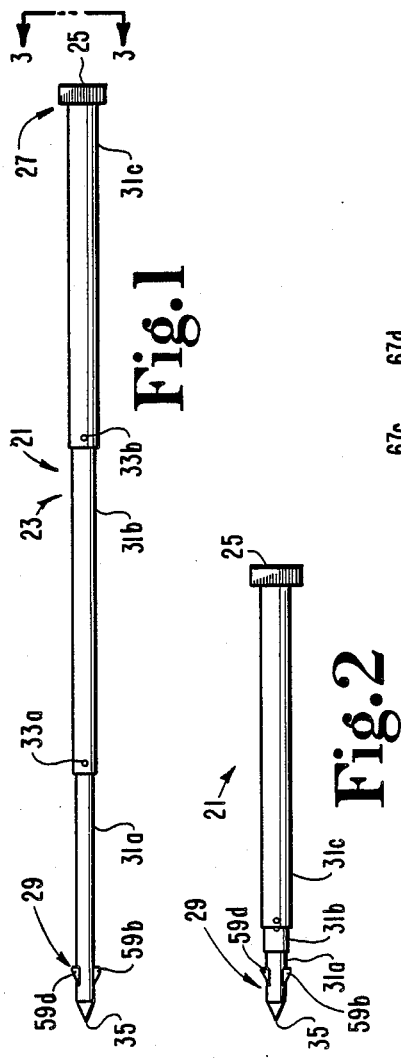
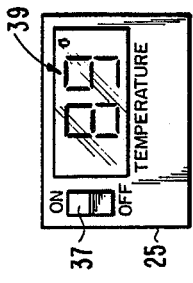
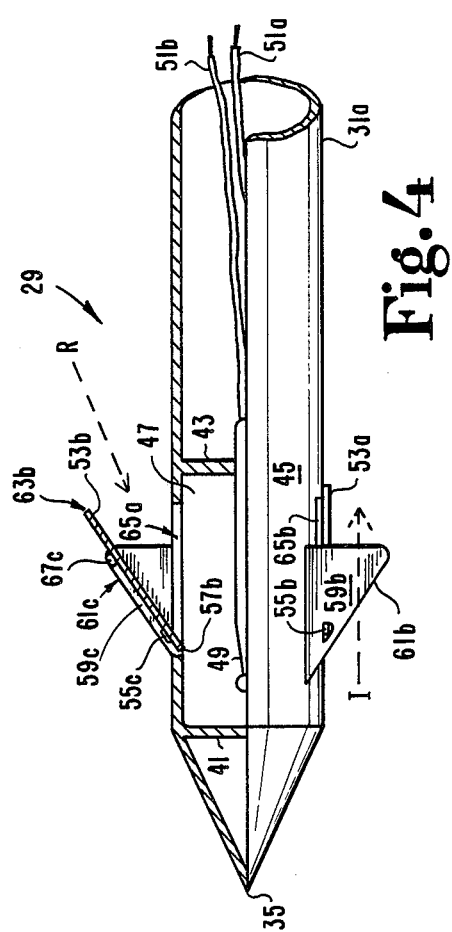
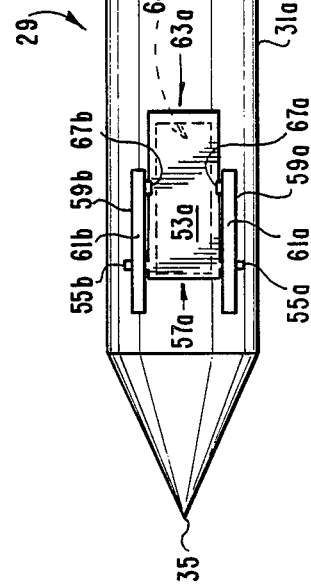
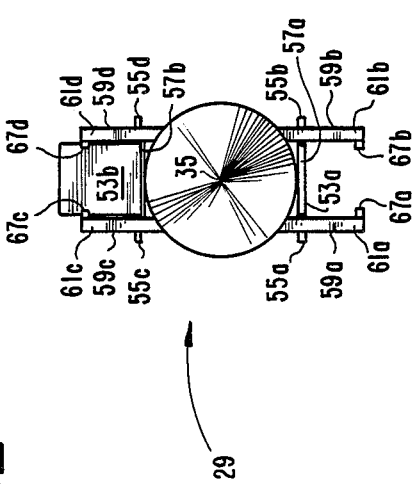
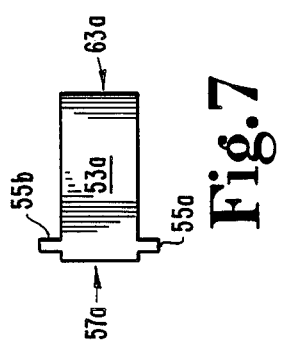

GRAIN PROBE

The present invention relates to probes for sampling and measuring the physical characteristics of stored agricultural grain.

BACKGROUND OF THE INVENTION

Agricultural grain, such as corn, wheat and the like, is typically stored in large bins of varying types after harvesting. It is known to be desirable for many reasons to sample stored grain and to measure various physical characteristics of the grain periodically at numerous and varied points in situ within bins of all types. Known devices for accomplishing these objectives include spear-like probes that are designed to be forcibly thrust into the grain at preselected points and to predetermined depths. Among the known spear-like probes are those that enable one to extract grain samples and to measure grain temperature, moisture content, or the like, in situ.

SUMMARY OF THE INVENTION

A principal object of the present invention is to provide a novel spear-like grain probe, with a novel grain probe tip, which provides for improved sampling and measuring of the physical characteristics of stored agricultural grain in situ.

One embodiment of the present invention is a grain probe for sampling and measuring the environmental characteristics of stored grain in situ, comprising a telescopic shaft having a meter fixedly attached to one end thereof and a grain probe tip fixedly attached to the opposite end thereof, a grain receiving chamber within the tip, an environmental measuring element affixed within the chamber and coupled to the meter, and means for automatically closing the chamber to grain kernels while the tip is being inserted into stored grain and automatically opening the chamber to grain kernels as the tip is being withdrawn from stored grain.

Another embodiment of the present invention is a grain probe for sampling stored grain in situ, comprising a rigid shaft having a grain probe tip fixedly attached to one end thereof, a grain receiving chamber within the tip, means for automatically closing the chamber to grain kernels while the tip is being inserted into stored grain and automatically opening the chamber to grain kernels as the tip is being withdrawn from stored grain, including at least one lateral opening in the tip communicating the chamber with the environs external to the tip, a pair of fins affixed to the tip on either side of the opening in parallel relationship and such that they are disposed longitudinally along the length of the shaft, a flap hingingly operable upon an axis running between and intersecting the fins, which flap is further operable to hingingly swing upon the axis to cover the opening and close the chamber to grain kernels as the tip is inserted into stored grain, thereby defining a closed chamber position, and to hingingly swing away from the tip and the opening upon the axis as the tip is withdrawn from stored grain, opening the chamber to grain kernels and thereby defining an open chamber position.

Another embodiment of the present invention is a grain probe for sampling and measuring the environmental characteristics of stored grain in situ, comprising a shaft having a meter fixedly attached to one end thereof and a grain probe tip fixedly attached to the opposite end thereof, a grain receiving chamber within the tip, an environmental measuring element affixed within the chamber and coupled to the meter, and means for automatically closing the chamber to grain kernels while the tip is being inserted into stored grain and automatically opening the chamber to grain kernels as the tip is being withdrawn from stored grain, including at least one lateral opening in the tip communicating the chamber with the environs external to the tip, a pair of fins affixed to the tip on either side of the opening in parallel relationship and such that they are disposed longitudinally along the length of the shaft, a flap hingingly operable upon an axis running between and intersecting the fins at points that are closer to the tip that to the meter, which flap is further operable to hingingly swing upon the axis to cover the opening and close the chamber to grain kernels as the tip is inserted into stored grain, thereby defining a closed chamber position, and to hingingly swing away from the tip and the opening upon the axis as the tip is withdrawn from stored grain, opening the chamber to grain kernels and thereby defining an open chamber position.

Another object of the present invention is to provide a novel spear-like grain probe that is readily collapsible into a compact storage position.

Related objects of the present invention will be clear to ordinary skilled artisans from the following description of the preferred embodiment.

BRIEF DESCRIPTION OF THE DRAWINGS

FIG. 1 is a side view of the most preferred embodiment of the grain probe of the present invention in the telescopically extended position.

FIG. 2 is a side view of the grain probe of FIG. 1 in a telescopically compacted position.

FIG. 3 is an enlarged rear view of the grain probe of FIG. 1 taken along line 3—3.

FIG. 4 is an enlarged and partially segmented side view of the most preferred grain probe tip of the present invention.

FIG. 5 is an enlarged bottom view of the grain probe tip of FIG. 4.

FIG. 6 is an enlarged front view of the grain probe tip of FIG. 4

FIG. 7 is an enlarged view of one of the flaps of the grain probe tip of FIG. 4.

DESCRIPTION OF THE PREFERRED EMBODIMENT

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to the drawings, there is shown in FIGS. 1-7 the most preferred grain probe 21 (FIGS. 1-3) and grain probe tip 29 (FIGS. 4-7) of the present invention. Grain probe 21 includes a shaft 23, a meter 25 fixedly attached to one end of shaft 23, and a grain probe tip 29 fixedly attached to the opposite end of shaft 23. In the most preferred embodiment of grain probe 21 of the present invention, shaft 23 is cylindrical and is composed of cylindrical shaft subsections 31a, 31b and 31c (FIGS. 1-2) that slide one within the other like the cylindrical sections of a hand telescope. As shown in FIGS. 1 and 2, shaft subsection 31a is sized and disposed to be telescopically received within subsection 31b, which in turn is sized and disposed to be telescopically received within subsection 31c. Subsections 31a, 31b and 31c of shaft 23 of the most preferred embodiment therefore permit shaft 23 to be telescoped between a fully extended position (FIG. 1) and a fully collapsed position (FIG. 2).

Subsection locks 33a and 33b, which are conventional spring biased buttons, lock the telescoping shaft subsections of shaft 23 against telescopic movement when shaft 23 is in the fully extended position (FIG. 1). Lock 33a is conventionally affixed to subsection 31a and is conventionally spring-biased radially outward therefrom so as to engage a correspondingly sized through hole in subsection 31b. Likewise, subsection lock 33b is affixed to subsection 31b and is spring biased radially outward therefrom to engage a corresponding through hole in subsection 31c. The operation of subsection locks 33a and 33b and the through holes of subsections 31b and 31c is similar to the conventional button locks found on telescoping tent pole subsections. Clearly, other suitable conventional locking means conventionally found on telescoping shaft subsections may be utilized, such as, for example, threaded, rotatable sheaths at the junction of the shaft subsections that actuate a camming element to lock the adjoining subsections with respect to each other. Such mechanisms may be found, for example, on conventional camera tripod legs, etc..

In the most preferred embodiment, shaft 23, and its corresponding subsections 31a, 31b, and 31c, are hollow, tubular members, preferably round, and are made of rigid material, such as noncorrosive metal, such as aluminum, or other corrosion resistant materials. Although shaft 23 of the most preferred embodiment, as shown in FIGS. 1 and 2, is made up of three subsections, the present invention may be practiced by using two shaft subsections, or more than three shaft subsections, depending on the length of shaft desired and the degree of storage compactness desired. Clearly, the present invention may be utilized with a single, nontelescoping shaft member in combination with other novel features of the present invention described below.

Turning to FIG. 3, there is illustrated meter 25 of the preferred embodiment, which includes an on/off switch 37 to activate the battery-powered digital display 39 of meter 25. Meter 25 is rigidly affixed to the end of shaft 23 opposite grain probe tip 29. Preferably, the digital display 39 of meter 25 is oriented in a plane normal to the longitudinal axis of shaft 23. In the preferred embodiment, meter 25 includes a battery powered ohmmeter that is coupled by wiring to a thermistor located in the grain probe tip (to be described below) to permit the measurement of the temperature of grain brought in contact with the grain probe tip. In the preferred embodiment, the ohmmeter of meter 25 is conventionally coupled to digital display 39 and is otherwise calibrated in the ways known in the art to directly display the ambient temperature in degrees stored grain in situ in direct proportion to the resistance measured by a thermistor located in the grain probe tip 29. Alternatively, meter 25 may be coupled to conventional circuitry known in the art that will directly display the ambient relative humidity of stored grain in situ as determined by conventional humidity sensors located in the grain probe tip 29.

In the preferred embodiment, digital display 39 preferably utilizes conventional light emitting diodes, providing the advantage of readability in a low light environment. However, readout 39 may also utilize conventional liquid crystal diodes. The digital display 39 is preferably large, advantageously providing easier reading than more standard needle-meter readouts. However, a needle-meter readout may be utilized when combined with other features of the present invention.

Referring now to FIGS. 4-7, there is shown the grain probe tip 29 of the most preferred embodiment, which is affixed to the end of shaft 23 opposite meter 25 (FIG. 1) and culminates with a conical end portion 35. Referring to FIG. 4, there is shown the partially segmented side view of the most preferred embodiment of the grain probe tip 29 of the present invention. Grain probe tip 29 is provided with spaced-apart interior bulkheads 41 and 43 disposed near the distal end of subsection 31a of shaft 23, and defining therebetween receiving chamber 47. Within receiving chamber 47 there is disposed a measuring element 49, the specific choice of which will depend upon the physical characteristic of the stored grain that is desired to be remotely measured. In the most preferred embodiment of the present invention, measuring element 49 is a conventional bead type thermistor for measuring the ambient temperature of stored grain in situ. Measuring element 49 is directly coupled to meter 25 by electrical wires 51aand 51b that extend from receiving chamber 47 through bulkhead 43, through shaft 23 subsections 31a, 31b, and 31c of the most preferred embodiment, and to meter 25. In a similar manner, other physical characteristics of stored grain in situ could be measured by selecting appropriate measuring elements 49 coupled to meter 25 in the manner taught to replace the bulb type thermistor and ohmmeter of the most preferred embodiment.

Referring to FIGS. 4-5, between bulkheads 41 and 43, wall 45 of subsection 31a of shaft 23 of the most preferred embodiment is provided with diametrically opposed openings 65a and 65b. Mounted externally to subsection 31a are hingingly operable flaps 53a and 53b, which are sized and disposed in relationship to openings 65a and 65b such that flaps 53a and 53b are operable to fully cover openings 65a and 65b respectively. Referring to FIGS. 4-6, flap 53a is shown in the closed position, whereas flap 53b is shown in the open position. Each flap 53a and 53b (FIG. 7) has two hinge tabs 55a and 55b, 55c and 55d, respectively, located near front ends 57a and 57b of flaps 53a and 53b, respectively. Hinge tabs 55a and 55b, and 55c and 55d of flaps 53a and 53b, respectively, are received into corresponding through holes (see FIG. 4) located in fins 59a, 59b, 59c and 59d, respectively, that are disposed on either side of openings 65a and 65b, respectively, and between which flaps 53a and 53b are hingingly operable in the manner described above. The hinge mechanisms provided by hinge tabs 55a, 55b, 55c and 55d may alternatively be any number of hinge types along the front edges of the door at front ends 57a and 57b so that the front end is fastened and hinges with respect to the probe tip and the rear ends are free of the probe tip and adapted to swing outwardly therefrom.

Fins 59a, 59b, 59c and 59d each have corresponding door tabs 67a, 67b, 67c and 67d that prevent flaps 53a and 53b, respectively, from being hingingly operable through more than about 30 degrees, as shown in FIG. 4, during removal of the grain probe. Each fin 59a, 59b, 59c and 59d is disposed such that its streamlining edge 61a, 61b, 61c and 61d, respectively, slope outwardly from subsection 31a toward the meter end of shaft 23, which coincides with the direction of indented insertion of the grain probe into scored grain. These streamlining edges facilitate insertion of the grain probe into stored grain by reducing frictional resistance and by preventing the dynamic flow of the grain during probe insertion from undesirably forcing open flaps 53a and 53b. Such flow is shown in FIG. 4 near door 53a as the phantom arrow labeled "I" for insertion. The dynamic insertion flow "I" helps keep flag 53a hingingly closed during grain probe insertion as is shown in FIG. 4. Fins 59a and 59b further function to keep grain kernels from wedging under the sides of flaps 53a and 53b during insertion and undesirably forcing them open. Fins 59a–d may be designed to have various geometries other than the flat thin-walled triangle structures shown in FIGS. 4–6, so long as they continue to function to direct flow of the grain kernels away from the sides of the flaps during insertion of the grain probe tip.

However, referring to FIG. 4, flap 53b is shown in the open position for complete illustration of both the open and closed flap modes. As the fully inserted grain probe of the most preferred embodiment is removed from stored grain, the dynamic removal flow "R" of the grain kernels (shown as phantom arrow "R" in FIG. 4) will open flaps 53a and 53b as grain kernels wedge under end portions 63a and 63b of flaps 53a and 53b, respectively. In the open position (flap 53b in FIG. 4), flaps 53a and 53b in cooperation with fins 61a, 61b, 61c, and 61d funnel grain kernels through openings 65a and 65b and into receiving chamber 47. Flow "R" in FIG. 4 is shown at an angle to depict the inward component of the grain flow into chamber 47. Initially, as the flaps are opening during the beginning withdrawal of the grain probe, the flow "R" is parallel and opposite to flow "I" shown in FIG. 4.

As can readily be seen, upon slight withdrawal of the fully inserted grain probe of the most preferred embodiment of the present invention, grain kernels located in close proximity to the fully inserted grain probe tip will be funneled into receiving chamber 47 and into direct contact with measuring element 49. Furthermore, the grain kernels first entrapped within receiving chamber 47 will remain therein through full withdrawal of the grain probe from the stored grain. The operator will thus have a sample of grain kernels from the proximate area into which the grain probe tip 29 was inserted.

A very rapid and accurate measurement of the physical characteristics of stored grain in situ may thus be obtained at the depth of insertion of the grain probe simply by inserting probe 29 to the depth desired and then removing the probe a few inches causing grain to come in direct contact with measuring element 49.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A grain probe for sampling and measuring the environmental characteristics of stored grain in situ, comprising:

a telescopic shaft having a meter fixedly attached to one end thereof and a grain probe tip fixedly attached to the opposite end thereof;
a grain receiving chamber within said tip;
an environmental measuring element affixed within said chamber and coupled to said meter; and
means for automatically closing said chamber to grain kernels while said tip is being inserted into stored grain and automatically opening said chamber to grain kernels as said tip is being withdrawn from stored grain, wherein said means for automatically opening and closing said chamber includes at least one lateral opening in said tip communicating said chamber with the environs external to said tip, a pair of fins affixed to said tip on either side of said opening in parallel relationship and such that they are disposed longitudinally along the length of said shaft, a flap hingingly operable upon an axis running between and intersecting said fins at points that are closer to said tip that to said meter, which flap is further operable to hingingly swing upon said axis to cover said opening and close said chamber to grain kernels as said tip is inserted into stored grain, thereby defining a closed chamber position, and to hingingly swing away from said tip and said opening upon said axis as said tip is withdrawn from stored grain, opening said chamber to grain kernels and thereby defining an open chamber position.

2. The grain probe of claim 1 and further comprising: means for restricting the hinged swing of said flap between said closed chamber position and said open chamber position to less than 45 degrees.

3. The grain probe of claim 2 wherein said fins each diverge outwardly from said tip in the direction of said meter.

4. A grain probe for sampling and measuring the environmental characteristics of stored grain in situ, comprising:

a telescopic shaft having a grain probe tip fixedly attached to one end thereof;
a grain receiving chamber within said tip;
an environmental measuring element affixed within said chamber and coupled to a meter; and
an opening in said tip for grain to flow into said receiving chamber, wherein said shaft includes a first shaft subsection and a second shaft subsection telescopically disposed with respect to each other, said first shaft subsection being thereby telescopically collapsible within said second shaft subsection from a fully expanded position of an expanded length to a fully compacted position having a telescopically compacted length substantially less than said expanded length.

5. The grain probe of claim 4 and further comprising means for locking said first shaft subsection against longitudinal movement with respect to said second shaft subsection when oriented into said extended position.

6. The grain probe of claim 5 and further comprising a third shaft subsection telescopically disposed with respect to said second shaft subsection collapsible from said expanded position to said compacted position.

7. The grain probe of claim 6 and further comprising means for locking said third shaft subsection against longitudinal movement with respect to said second shaft subsection when oriented into said expanded position.

8. The grain probe of claim 4 having said meter fixedly attached to one end of said shaft, and including means for automatically closing said chamber to grain kernels while said tip is being inserted into stored grain and automatically opening said chamber to grain kernels as said tip is being withdrawn from stored grain.

9. A grain probe for sampling stored grain in situ, comprising:

a rigid shaft having a grain probe tip fixedly attached to one end thereof;

a grain receiving chamber within said tip;

means for automatically closing said chamber to grain kernels while said tip is being inserted into stored grain and automatically opening said chamber to grain kernels as said tip is being withdrawn from stored grain, including at least one lateral opening in said tip communicating said chamber with the environs external to said tip, a pair of fins affixed to said tip on either side of said opening in parallel relationship and such that they are disposed longitudinally along the length of said shaft, a flap hingingly operable upon an axis running between and intersecting said fins, which flap is further operable to hingingly swing upon said axis to cover said opening and close said chamber to grain kernels as said tip is inserted into stored grain, thereby defining a closed chamber position, and to hingingly swing away from said tip and said opening upon said axis as said tip is withdrawn from stored grain, opening said chamber to grain kernels and thereby defining an open chamber position.

10. The grain probe of claim 9 and further comprising:

means for restricting the hinged swing of said flap between said closed chamber position and said open chamber position to less than 45 degrees.

11. The grain probe of claim 10 wherein said fins each diverge outwardly from said tip in a longitudinal direction away therefrom.

12. A grain probe for sampling and measuring the environmental characteristics of stored grain in situ, comprising:

a shaft having a meter fixedly attached to one end thereof and a grain probe tip fixedly attached to the opposite end thereof;

a grain receiving chamber within said tip;

an environmental measuring element affixed within said chamber and coupled to said meter; and means for automatically closing said chamber to grain kernels while said tip is being inserted into stored grain and automatically opening said chamber to grain kernels as said tip is being withdrawn from stored grain, including at least one lateral opening in said tip communicating said chamber with the environs external to said tip, a pair of fins affixed to said tip on either side of said opening in parallel relationship and such that they are disposed longitudinally along the length of said shaft, a flap hingingly operable upon an axis running between and intersecting said fins at points that are closer to said tip that to said meter, which flap is further operable to hingingly swing upon said axis to cover said opening and close said chamber to grain kernels as said tip is inserted into stored grain, thereby defining a closed chamber position, and to hingingly swing away from said tip and said opening upon said axis as said tip is withdrawn from stored grain, opening said chamber to grain kernels and thereby defining an open chamber position.

13. The grain probe of claim 12 and further comprising:

means for restricting the hinged swing of said flap between said closed chamber position and said open chamber position to less than 45 degrees.

14. The grain probe of claim 12 wherein said fins each diverge outwardly from said tip in the direction of said meter.

15. The grain probe of claim 12 wherein said environmental measuring element is a thermistor.

16. The grain probe of claim 15 wherein said meter is a digital display ohmmeter calibrated to display temperature in degrees as determined at said thermistor.

* * * * *